United States Patent [19]
Bell

[11] Patent Number: 4,547,909
[45] Date of Patent: Oct. 22, 1985

[54] EYE PROTECTION MEANS FOR EYE WEAR

[76] Inventor: Michael Bell, P.O. Box 400, Warrington, Pa. 18976

[21] Appl. No.: 552,999

[22] Filed: Nov. 17, 1983

[51] Int. Cl.⁴ ............................................. A61F 9/02
[52] U.S. Cl. ........................................ 2/431; 2/449; 351/158
[58] Field of Search ................... 2/431, 426, 432, 442, 2/443, 448, 449, 440, 441, 422, 12; 351/158

[56] References Cited
U.S. PATENT DOCUMENTS

| 2,446,048 | 7/1948 | Kimball | 2/440 |
| 2,511,329 | 6/1950 | Craig | 2/12 X |
| 2,920,327 | 1/1960 | Singer | 2/431 |
| 4,076,373 | 2/1978 | Moretti | 2/434 X |

FOREIGN PATENT DOCUMENTS 0753789 11/1965 Canada .................... 2/449

OTHER PUBLICATIONS

Advertisement of safety glasses, Fendall Company, 5 E. College Drive, Arlington Heights, IL 60004.

Primary Examiner—Peter Nerbun
Attorney, Agent, or Firm—Caesar, Rivise, Bernstein & Cohen, Ltd.

[57] ABSTRACT

Eye protection means for use in combination with eye wear, such as safety glasses, having a brow guard in the form of a surface extending from the upper portion of the eye wear to a portion closely adjacent to the brow of the wearer. In one embodiment of the invention the eye protection means comprises magnetic dust collecting means formed of a ferromagnetic material for securement to the brow guard and arranged so that airborn dust particles falling thereon become trapped thereon, thereby decreasing the potential for entering the eye of the wearer. In another embodiment the dust collecting means comprises at least one layer of material arranged to be secured to the brow guard of the safety glasses and having an adhesive upper surface arranged to trap air-born dust particles falling thereon so as to decrease the potential for such particles entering the eye of the wearer.

11 Claims, 5 Drawing Figures

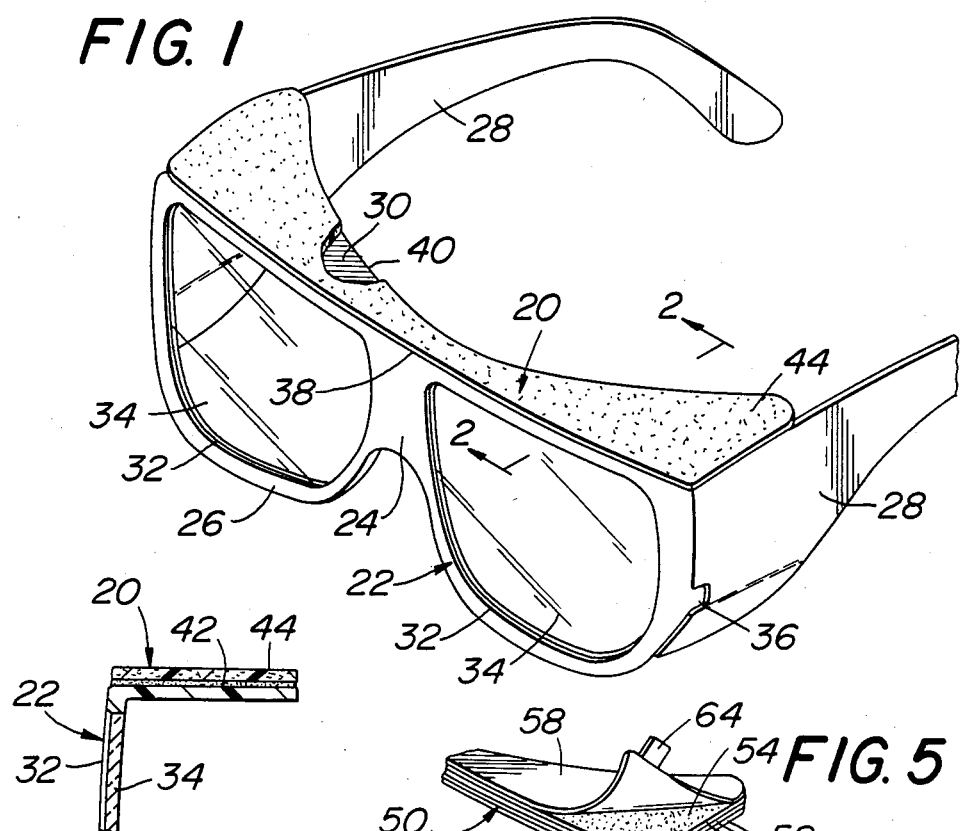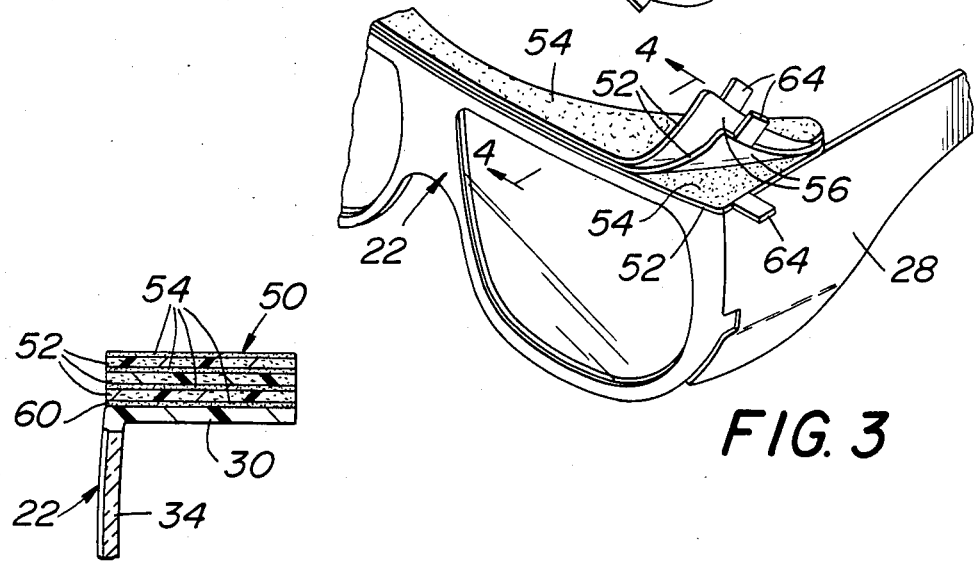

EYE PROTECTION MEANS FOR EYE WEARFPG,3

BACKGROUND OF THE INVENTION

This invention relates generally to eye wear and more particularly to eye protection means for use in combination with eye glasses, spectacles or goggles.

Various industrial environments are characterized by a high degree of air-borne dust particles in the ambient atmosphere. Such particles present an obvious occular hazard to unprotected personnel. While safety goggles may provide some measure of protection against air-borne particles, their main advantage is in protecting the eye from flying debris, etc. Thus, floating air-borne particles, particularly if of a fine size, may be so all pervasive as to float around the periphery of the eye glasses or goggles and gain ingress to the eye.

The Fendall Company of Arlington Heights, Ill. has offered for sale safety glasses which include small magnetic inserts on the temple pieces of the eye glass frame. The inserts are designed to attract dust particles thereto and away from the wearer's eyes. While such glasses may be suitable for trapping some ferromagnetic particles, the location of the magnetic areas on the temples significantly restricts effectiveness of the dust trapping action. In this regard with magnetic inserts located on the temples those air-borne particles which would tend to enter the eye through the space between the wearer's brow and the frame or the top edge of the glasses may not be diverted to the temple pieces due to their remoteness. In order to insure sufficient attraction of the particles to the remotely located temples from the brow, large or powerful and relatively expensive magnetics must be utilized. Needless to say use of such magnets is undesireable from the standpoints of cost, comfort, appearance, etc.

Accordingly, it is the general object of the instant invention to provide effective eye protection means for use with glasses and which overcomes the disadvantges of the prior art.

It is the further object of the instant invention to provide eye protection means which is effective for trapping air-borne ferromagnetic particles, to preclude the same from gaining ingress to the eye.

While air-borne magnetic particles represent a significant hazard to the eye, such particles form only a small portion of air-borne dust particles which can present an occular hazard. In this regard many industrial environments are characterized by significant levels of non-ferrous air-borne dust particles. Examples of such environments are found in textile mills, lumber mills, etc., where cotton, wood or other non-ferrous dust may permeate the air. In such applications the use of magnetic means is ineffectual for trapping the air-borne dust particles.

Accordingly, it is a further object of the instant invention to provide eye protection means for use with glasses, spectacles or goggles and which is effective for trapping non-ferrous dust particles.

These and other objects of the instant invention are achieved by providing eye protection means for use in combination with safety glasses having a brow guard in the form of a surface extending from the upper portion of the lenses of the glasses to a position closely adjacent to the brow of the wearer. In each embodiment of the invention the eye protection means comprises dust collecting means disposed on the brow portion and being formed of a dust retentive composition, whereupon air-borne dust particles falling thereon becomes trapped so as to decrease the potential for entering the eye of the wearer. In one embodiment the dust retentive means comprises magnetic material for trapping ferromagnetic particles. In an other embodiment the dust retentive means comprises at least one this layer of a material having a tacky exterior surface for trapping the dust particles thereon.

Other objects and many of the attendant advantagess of this invention will be readily appreciated as the same becomes better understood by reference to the following detailed description when considered with the accompanying drawings wherein:

FIG. 1 is a perspective view of a conventional pair of safety glasses, including one embodiment of the eye protection means of the instant invention;

FIG. 2 is an enlarged sectional view taken along line 2—2 of FIG. 1;

FIG. 3 is a perspective view of a portion of the safety glasses shown in FIG. 1, but including a second embodiment of the eye protection means of the subject invention;

FIG. 4 is an enlarged sectional view taken along line 4—4 of FIG. 3;

FIG. 5 is a perspective view of a portion of the eye protection means showing the embodiment in FIG. 3 before securement to the safety glasses.

Referring now to the various figures of the drawing wherein like reference characters refer to like parts, there is shown in FIG. 1 a conventional pair of safety glasses 22 to which is secured one embodiment of an eye protection device 20 of the subject invention.

Before describing the details of the eye protection means of this invention a brief description of the safety goggles 22 is in order. Basically the glasses comprise a plastic frame 24 having a front or lens holding portion 26, a pair of temple pieces 28 and a brow guard 30. The front portion 26 includes a pair of openings 32 into which a pair of spectacle lenses 34 (either prescription or non-prescription) are disposed. The temple pieces 28 are pivotably secured at hinge 36 located at respective sides of the front portion 26. The brow guard 30 extends along the top edge 38 of the front portion 26 of the goggles and is configured so that its peripheral edge 40 is disposed immediately adjacent to the brow of the wearer when the glasses are in place.

The eye protection means 20 of the embodiment shown in FIG. 1 basically comprise a thin flexible strip formed of a plastic material having ferromagnetic properties, i.e., being magnetic, and whose profile is shaped to conform to the periphery of the brow portion 30 of the glasses to cover the entire top surface of the brow portion 30. The underside of the strip 20 includes an adhesive surface 42. The adhesive surface 42 serves as the means for fixedly securing the strip 20 to the brow guard to holding it in place.

When eye protection means 20 is located in place on the brow guard and the glasses are worn, air-borne particles which would tend to attempt ingress to the eye from the space between the brow guard and the brow of the wearer will be trapped on the top surface 44 of the eye protection means. In order to rid the means of the adhered ferromagnetic particles when it becomes loaded, all that is necessary is to wipe the particles off the top surface of the means 20.

As will thus be appreciated from the foregoing the eye protection means 20 of the embodiment shown in FIG. 1 is of considerable utility and effectiveness for protecting the eye of the wearer in conditions having air-borne ferromagnetic particles. In applications where the air-borne particles are not ferromagnetic the eye protection means forming the second embodiment of this invention to be described hereinafter should be utilized.

Thus, in FIG. 3 the eye protection means for use in nonferromagnetic dust situations is shown. That means is denoted by the reference numeral 50 and is arranged to be used on the glasses 22 described heretofor. Thus, the details of glasses 22 need not reiterated hereinafter.

The means 50 basically comprises a stack of plural dust trapping layers 52. The stack 50 is shaped so that it completely covers the brow guard 30. Each of the layers 50 comprises an upper surface 54 and a lower surface 56. The upper surface 54 of each layer includes an adhesive thereon. Thus, the stack is held together by the adhesive upper surface 54 of an underlying layer making contact with the underside surface 56 of the layer disposed immediately above it. A readily peelable protective cover sheet 58 is disposed on the top surface 54 of the topmost layer of the stack. The bottommost layer of the stack also includes an adhesive layer on its underside surface 56. This adhesive layer is denoted by the reference numeral 60 (FIG. 4) and serves as the means for securing the stack to the brow guard 30. A protective cover sheet 62, similar to cover sheet 58, is disposed temporarily on the undersurface 60 of the bottommost layer of the stack.

The cover sheets 58 and 62 serve as the means for protecting the adhesive layers of the associated portions of the stack until the stack 50 is ready for mounting and use on the glasses 22. Each layer of the stack as well as the two cover sheets includes a finger grasping tab 64 projecting from the marginal edge of the stack. Each tab 64 serves as a convenient means for enabling the peeling of the associated layer from the remaining portion of the stack.

In accordance with the preferred embodiment of the invention shown in FIG. 3 each layer 52 is formed of a very thin, flexible material, such a Mylar, so that the stack can include multiple layers, e.g. 10, and yet be quite thin and non-bulky. Other materials can be used for the layers, such as paper stock, and the like.

The use of the stack 50 is as follows:

The bottom cover sheet 62 is peeled off of the stack by grasping its tab portion 64, thereby exposing the underside adhesive layer 60. The stack is then disposed on the brow guard 30 of the goggles so that the underside adhesive 60 contacts the top surface of the brow guard, thereby securing the stack in place. When the glasses are ready to be worn in a dusty environment the protective cover sheet 58 is peeled off the top layer 52 the stack, thereby exposing the adhesive surface 54 of the top layer. The exposed adhesive surface acts to trap and hold any dust particles falling thereon. Accordingly, any dust particles which would have landed on the brow guard and attempted to gain access around the brow guard and into the eye will be trapped and held in place on the adhesive surface of the top layer. After the top layer has trapped a substantial amount of dust particles so that it no longers offers exposed adhesive portions the user then peels the top layer 52 off of the stack 50 by grasping its tab 64, thereby exposing the fresh adhesive layer 54 of the underlying layer 52. The adhesive forming the underside layer 60 of the stack is selected so as to be peelable to enable the lowermost layer 52 to be peeled off the brow guard after its top adhesive surface 54 is full of dust particles to enable a completely new stack 52 be secured to the brow guard 30.

As will be appreciated from the foregoing the eye protection means of the subject invention are simple in construction, can be manufactured at low cost and offer a high degree of protection to the eye by trapping various types of air-borne dust particles thereon.

Without further elaboration, for foregoing will so fully illustrate my invention that others may, by applying current or future knowledge, readily adapt the same for use under various conditions of service.

I claim:

1. Eye protection means for use in combination with eye wear, said eye wear having at least one lens and a brow guard in the form of a surface extending laterally inwardly from the upper portion of the eye wear lens over to a position closely adjacent to the brow of the wearer, a dust retentive means in the form of a stack of plural layers of thin material secured to said brow guard, each of said layers having a tacky outer surface and being releasably secured to the underlying layer, whereupon said topmost layer traps dust particles thereon and when full said topmost layer is removed from the stack to expose the tacky surface of the underlying layer to permit said layer to trap air-borne dust particles thereon.

2. The eye protection means of claim 1 wherein said lowermost layer has an adhesive undersurface for securement to said brow guard.

3. The eye protection means of claim 1 wherein said thin layers are formed of a paper stock.

4. The eye protection means of claim 1 wherein said thin layers are formed of a plastic material.

5. The eye protection means of claim 4 wherein said material is Mylar.

6. The eye protection means of claim 1 wherein said stack is configured to conform to the profile of said brow guard.

7. The eye protection means of claim 1 additionally comprising a readily releasable cover layer on said top layer to protect the tacky surface thereof until said eye protection means is ready for use.

8. The eye protection means of claim 7 wherein the lowermost layer includes an adhesive surface for securement to said one surface to mount said eye protection means in place, said adhesive surface on said lowermost layer including a readily releaseable cover layer thereon to protect said surface until said eye protection means is to be mounted on said brow guard.

9. The eye protection means of claim 1 wherein each of said layers includes a grasping portion for facilitating the removal of the layer from the stack.

10. The eye protection means of claim 9 wherein said grasping means comprises a projecting tab.

11. Eye protection means for use in combination with eye wear, said eye wear having a lens portion and a first portion located adjacent said lens portion, said first portion including a first surface, said eye protection means comprising dust retentive means in the form of a stack of plural layers of thin material secured to said first surface, each of said layers having a tacky outer surface and being releasably secured to the underlying layer, whereupon said topmost layer traps dust particles thereon and when full said topmost layer is removed from the stack to expose the tacky surface of the underlying layer to permit said layer to trap airborne dust particles thereon.

* * * * *